United States Patent [19]

Rohr

[11] 4,417,919

[45] Nov. 29, 1983

[54] 3-HALOALKOXY-4-NITRO-2'-CHLORO-4'-TRIFLUOROMETHYLDIPHENYL ETHERS AND HERBICIDAL USE THEREOF

[75] Inventor: Otto Rohr, Therwil, Switzerland

[73] Assignee: Ciba-Geigy Corporation, Ardsley, N.Y.

[21] Appl. No.: 347,400

[22] Filed: Feb. 10, 1982

[30] Foreign Application Priority Data

Feb. 19, 1981 [CH] Switzerland ..................... 1106/81

[51] Int. Cl.³ ................... A01N 31/00; C07C 43/263
[52] U.S. Cl. ...................................... 71/124; 568/586
[58] Field of Search ........................ 568/586; 71/124

[56] References Cited

U.S. PATENT DOCUMENTS

| | | | |
|---|---|---|---|
| 4,093,446 | 6/1978 | Bayer et al. | ............ 568/586 X |
| 4,220,468 | 9/1980 | Bayer et al. | ............ 568/586 X |
| 4,264,777 | 4/1981 | Yoshimoto et al. | ............ 568/586 |

Primary Examiner—Bernard Helfin
Attorney, Agent, or Firm—Frederick H. Rabin

[57] ABSTRACT

The invention relates to novel 3-haloalkoxy-4-nitro-2'-chloro-4'-trifluoromethyl-diphenyl ethers with herbicidal properties. These compounds have good selectivity in different crops of useful plants, e.g. cereals, rice, cotton and, in particular, soybeans and maize. The novel compounds have the formula I

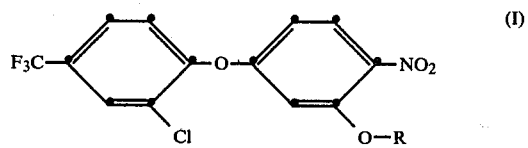

(I)

wherein R is difluoromethyl or 2-chloro-1,1,2-trifluoroethyl.

6 Claims, No Drawings

3-HALOALKOXY-4-NITRO-2'-CHLORO-4'-TRIFLUOROMETHYLDIPHENYL ETHERS AND HERBICIDAL USE THEREOF

The present invention relates to novel 3-haloalkoxy-4-nitro-2'-trifluoromethyldiphenyl ethers with selective herbicidal properties, to the production thereof, to compositions containing them, and to a method of selectively controlling weeds in crops of cereals, rice, cotton and, in particular, maize and soybeans.

Herbicidally active diphenyl ethers have long been known and some are commercially available. 2'-Chloro-4-nitrodiphenyl ethers are described e.g. in U.S. Pat. Nos. 4,220,468 and in Japanese patent publication 75 69 227. Such compounds have been proposed as herbicides and used in actual practice in order to facilitate agricultural work and to increase the productivity of useful plants in agriculture and horticulture.

However, there is still a need to find novel herbicides which have superior herbicidal properties. Herbicides intended for use in agruculture and horticulture are preferably compounds which selectively control the target weeds without being toxic to the useful plants. Known herbicides do not always have these beneficial properties.

Surprisingly, it has now been found that the novel compounds of this invention are superior in selective weed control to the products introduced onto the market and to the structurally most closely related compounds of the patent literature.

The 3-haloalkoxy-4-nitro-2'-chloro-4'-trifluoromethyl-diphenyl ethers of the present invention have the general formula I

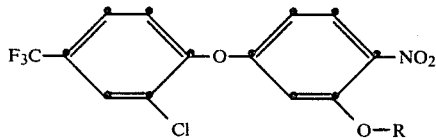
(I)

wherein R is difluoromethyl or 2-chloro-1,1,2-trifluoroethyl.

The following individual compounds fall under formula I: 2'-chloro-3-difluoromethoxy-4'-trifluoromethyl-4-nitrodiphenyl ether and 3-(2-chloro-1,1,2-trifluoroethoxy)-2'-chloro-4'-trifluoromethyl-4-nitro-diphenyl ether.

The novel diphenyl ethers of the formula I are obtained by the processes described below.

A first process for obtaining the compounds of formula I comprises reacting the phenoxyphenol of the formula II

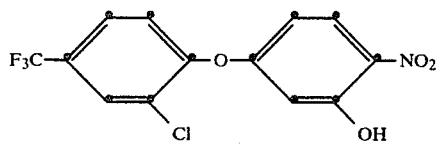
(II)

optionally in the presence of a base and in an inert solvent, with a haloalkane of the formula III Hal—R  (III)

wherein R is as defined for formula I and Hal is chlorine, bromine or iodine.

The compound of the formula I, wherein R is the 2-chloro-1,1,2-trifluoroethyl radical, is obtained by a second process which comprises reacting the phenoxyphenol of the formula II, in the presence of a base and in an inert organic solvent, optionally under elevated pressure, with chlorotrifluoroethane.

The first process is conveniently carried out in the temperature range from 20° to 150° C., preferably from 50° to 100° C., under normal pressure. Suitable solvents are water or mixtures of water and organic solvents such as ethers, e.g. tetrahydrofuran, dioxan; alcohols, e.g. methanol, ethanol, isopropanol; acid amides, e.g. dimethyl formamide, 2-pyrrolidinone, hexamethylphosphoric triamide, acetonitrile or dimethyl sulfoxide; or also the organic solvents themselves. Examples of suitable bases are hydroxides such as sodium and potassium hydroxide, or hydrides such as sodium or calcium hydride.

The second process is advantageously carried out in the temperature range from 20° to 150° C., preferably from 40° to 100° C., under pressures from 10 to 50 bar, preferably from 1 to 12 bar. Examples of suitable polar, aprotic solvents are dimethyl formamide, 2-pyrrolidinone, hexamethylphosphoric triamide, acetonitrile or dimethyl sulfoxide. Examples of suitable bases are sodium and potassium hydroxide, sodium and calcium hydride, sodium amide or lithium diisopropylamide.

The starting compound of the formula II is described in U.S. Pat. No. 4,220,468, and that of the formula III is commercially available.

The compounds of the invention are stable under normal conditions. No special precautionary measures are necessary for handling them.

The compounds of formula I have selective herbicidal properties which make them particularly suitable for controlling monocot and dicot weeds in crops of cereals, rice, cotton and, in particular, maize and soybeans. Accordingly, the invention also relates to herbicidal compositions which contain a compound of the formula I, and to methods of pre- and postemergence weed control.

The compounds of the formula I are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polmyer substances. Just like the nature of the compositions, the methods of application, such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane, or paraffins, alcohols and glycols and their ethers and esters, such as ethanol, ethylene glycol, ethylene glycol monomethyl or monoethyl ether; ketones such as cyclohexanone, strongly polar solvents such as N-methyl-2-pyrrolidone, dimethyl sulfoxide or dimethyl formamide; as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispered silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali, alkaline earth or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali salts, alkaline earth salts or unsubstituted or substituted ammonium salts and contain a $C_8$–$C_{22}$ alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 glycol units per propylene glycol unit.

Representative examples of non-ionic surfactants are nonylphenol-polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one polyglycol ether or $C_8$–$C_{22}$ alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyl di-(2-chloroethyl)ethylammonium bromide.

The surfactants customarily employed in the art of formulation are described e.g. in the following publications: "McCutcheon's Detergents and Emulsifiers Annual", MC Publishing Corp., Ringwood, New Jersey, 1979; Sisely and Wood, "Encyclopedia of Surface Active Agents", Chemical Publishing Co. Inc., New York 1964.

The pesticidal formulations will normally contain 0.1 to 99%, preferably 0.1 to 95%, of a compound of the formula I, 1 to 99% of a solid or liquid adjuvant, and 0 to 30%, preferably 0.1 to 25%, of a surfactant.

Preferred formulations are composed in particular of the following constituents (%=percentage by weight):

Solutions active ingredient: 5 to 95%, preferably 10 to 80%
solvent: 95 to 5%, preferably 90 to 0%
surfactants: 1 to 30%, preferably 2 to 20%

Emulsifiable concentrates active ingredient: 10 to 50%, preferably 10 to 40%
surfactant: 5 to 30%, preferably 10 to 20%
liquid carrier: 20 to 95%. preferably 40 to 80%

Dusts active ingredient: 0.5 to 10%, preferably 2 to 8%
solid carrier: 99.5 to 90%, preferably 98 to 92%

Suspension concentrates active ingredient: 5 to 75%, preferably 10 to 50%
water: 94 to 25%, preferably 90 to 30%
surfactant: 1 to 30%, preferably 2 to 25%

Wettable powders active ingredient: 5to 90%, preferably 10 to 80%, and most preferably, 20 to 60%,
surfactant: 0.5 to 20%, preferably 1 to 15%
solid carrier: 5 to 90%, preferably 30 to 70%

Granulates active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally 0.1 to 10 kg a.i./ha, preferably 0.25 to 5 kg a.i./ha.

The compositions can also contain further ingredients such as stabilisers, antifoams, viscosity regulators, binders, adhesives, as well as fertilisers or other active compounds, in order to attain special effects.

The following Examples illustrate the invention. Pressures are given in millibars (mbar).

Preparatory Examples

Example 1:

Preparation of 2'-chloro-3-difluoromethoxy-4'-trifluoromethyl-4-nitrodiphenyl ether

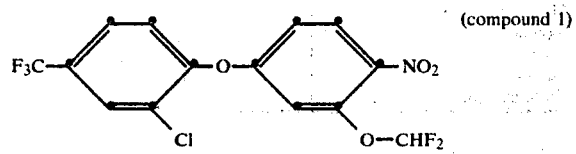

(compound 1)

with efficient stirring, 15 ml of 30% aqueous sodium hydroxide solution are added to a solution of 33.4 g of 2'-chloro-3-hydroxy-4'-trifluoromethyl-4-nitrodiphenyl ether in 100 ml of dioxan and the mixture is heated to 70°–75° C. Gaseous chlorodifluoromethane is then passed into the reaction mixture for 1 hour. The solution is then cooled, diluted with 350 ml of water and extracted with ethyl acetate. The organic phase is concentrated, to give 35.4 g of 2'-chloro-3-difluoromethoxy-4'-trifluoromethyl-4-nitrodiphenyl ether in the form of a yellow oil; $n_D^{22}$: 1.5315.

calculated: C 43.83%; H 1.84%; N 3.65%; F 24.76%
found: C 43.8%; H 2.0%; N 3.8%; F 24.6%.

Example 2:

Preparation of 3-(2-chloro-1,1,2-trifluoroethoxy)-2'-chloro-4'-trifluoromethyl-4-nitrodiphenyl ether

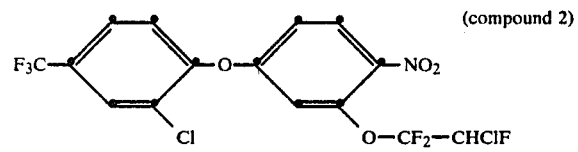

(compound 2)

25.4 g of gaseous chlorotrifluoroethane are introduced under pressure into a solution of 33.4 g of 2'-chloro-3-hydroxy-4'-trifluoromethyl-4-nitrodiphenyl ether and 6.5 g of potassium hydroxide in 100 ml of dimethyl formamide in a 300 ml pressure vessel. With efficient stirring, the reaction mixture is heated for 8 hours to 60° C., the pressure rising to 10 bar. Thereafter the reaction mixture is poured into ice-water and extracted with methylene chloride. The organic phase is concentrated and the residue is distilled in a bulb tube, giving 37 g of 3-(2-chloro-1,1,2-trifluoroethoxy)-2'-chloro-4'-trifluoromethyl-4-nitrodiphenyl ether in the form of a yellow oil. Boiling point: 150° C./0.001 mbar.

Formulation Examples

Example 3

Formulation Examples for active ingredients of the formula I (throughout, percentages are by weight)

| (a) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentration by dilution with water.

| (b) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

| (c) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Biological Examples

Example 4

Preemergence herbicidal action

In a greenhouse, immediately after sowing the test plants in seed dishes, the surface of the soil is treated with an aqueous dispersion of test compound, obtained from a 25% emulsifiable concentrate. Concentrations of 0.25 to 4 kg of active ingredient per hectare are used. The seed dishes are kept in the greenhouse at 22°–25° C. and 50–70% relative humidity, and the test is evaluated after 3 weeks in accordance with the following rating:
1 = plants totally withered
2–3 = very pronounced action 4-6 = medium action
7-8 = insignificant action
9 = no action (as untreated controls)

| Action rate of application kg a.i./ha | Compound 1 | | | Compound 2 | | |
|---|---|---|---|---|---|---|
| Test plants | 1 | 0.5 | 0.25 | 4 | 2 | 1 |
| barley | 7 | 9 | 9 | — | — | — |
| wheat | 2 | 7 | 9 | 3 | 8 | 9 |
| maize | 8 | 9 | 9 | 9 | 9 | 9 |
| dry rice | 4 | 4 | 7 | 7 | 9 | 9 |
| Avena fatua | 1 | 2 | 2 | 2 | 3 | 8 |
| Bromus tectorum | 1 | 2 | 2 | — | — | — |
| Lolium perenne | 1 | 1 | 2 | — | — | — |
| Alopecurus myos. | 1 | 1 | 2 | 1 | 1 | 1 |
| Digitaria sang. | 1 | 1 | 1 | — | — | — |
| Echinochloa c.g. | 1 | 1 | 1 | 1 | 3 | 8 |
| Sorghum halep. | 1 | 1 | 1 | — | — | — |
| Rottboellia ex. | 1 | 1 | 2 | 2 | 4 | 9 |
| soybeans | 7 | 9 | 9 | 9 | 9 | 9 |
| cotton | 8 | 9 | 9 | 2 | 3 | 9 |
| Abutilon | 1 | 1 | 1 | 1 | 1 | 3 |
| Sida spinosa | 1 | 1 | 1 | — | — | — |
| Amaranthus ret. | 1 | 1 | 1 | — | — | — |
| Chenopodium Sp. | 1 | 1 | 1 | 1 | 1 | 3 |
| Solanum nigrum | 1 | 1 | 1 | — | — | — |
| Chrysanthe. leuc. | 1 | 1 | 1 | — | — | — |
| Viola tricolor | 1 | 1 | 1 | 1 | 1 | 1 |
| Veronica Sp. | 1 | 1 | 1 | — | — | — |

Example 5:

Postemergence herbicidal action (contact herbicide)

A number of weeds in pots, both monocots and dicots, are sprayed postemergence, in the 4- to 6-leaf stage, with an aqueous active ingredient dispersion at a rate of application of 0.5 to 2 kg a.i./ha, and then kept at 24°-26° C. and 45-60% relative humidity. The test is evaluated at least 15 days after treatment and the results are assessed in accordance with the same rating as in the preemergence test (Example 4).

| Action rate of application kg a.i./ha | Compound 1 | | | Compound 2 | | |
|---|---|---|---|---|---|---|
| Test plants | 2 | 1 | 0.5 | 2 | 1 | 0.5 |
| wheat | 1 | 1 | 4 | 2 | 2 | 4 |
| maize | 2 | 3 | 4 | 4 | 4 | 7 |
| dry rice | 3 | 4 | 4 | 4 | 5 | 6 |
| Avena fatua | 1 | 1 | 2 | 2 | 2 | 6 |
| Alopecurus myos. | 1 | 1 | 2 | 2 | 3 | 3 |
| Echinochloa c.g. | 1 | 1 | 2 | 2 | 2 | 3 |
| soybeans | 1 | 2 | 2 | 6 | 7 | 8 |
| cotton | 1 | 1 | 2 | 1 | 1 | 1 |
| Abutilon | 1 | 1 | 1 | 1 | 1 | 1 |
| Xanthium Sp. | 1 | 1 | 4 | 2 | 2 | 3 |
| Chenopodium Sp. | 1 | 1 | 2 | 1 | 1 | 2 |
| Ipomoea | 1 | 1 | 1 | 1 | 1 | 1 |
| Sinapis | 1 | 1 | 1 | 1 | 2 | 2 |
| Galium aparine | 1 | 1 | 1 | 1 | 1 | 1 |
| Viola tricolor | 1 | 1 | 1 | 1 | 1 | 1 |

What is claimed is:
1. 3-Difluoromethoxy-4-nitro-2'-chloro-4'-trifluoromethyldiphenyl ether.
2. A herbicidal composition which contains, as active ingredient, the compound according to claim 1, together with an agriculturally suitable carrier therefor.
3. A method of controlling unwanted plant growth, which comprises applying to the unwanted plants or to the locus thereof a herbicidally effective amount of the compound according to claim 1.
4. A method according to claim 3 for the selective control of monocot and dicot weeds in crops of useful plants.
5. A method according to claim 4, wherein the crop is soybeans.
6. A method according to claim 4, wherein the crop is maize.

* * * * *